United States Patent [19]
Schäfer et al.

[11] Patent Number: 5,643,261
[45] Date of Patent: Jul. 1, 1997

[54] OSTEOSYNTHESIS DEVICE

[75] Inventors: Bernd Schäfer, Schorndorf; Klaus Zielke, Bad Wildungen, both of Germany

[73] Assignee: Schafer micomed GmbH, Germany

[21] Appl. No.: 400,252

[22] Filed: Mar. 8, 1995

[30] Foreign Application Priority Data

Mar. 10, 1994 [DE] Germany .......................... 44 07 975.3
Mar. 18, 1994 [DE] Germany .......................... 44 09 242.3

[51] Int. Cl.⁶ .................................................. A61B 17/70
[52] U.S. Cl. .................... 606/61; 606/60; 606/69; 606/72
[58] Field of Search ...................... 606/61, 69, 70, 606/71, 73, 60, 54; 623/17

[56] References Cited

U.S. PATENT DOCUMENTS 5,042,982  8/1991  Harms et al. .......................... 606/61
5,352,224  10/1994  Westermann .......................... 606/61

Primary Examiner—Michael Buiz
Assistant Examiner—David O. Reip
Attorney, Agent, or Firm—Jones, Tullar & Cooper, P.C.

[57] ABSTRACT

In an osteosynthesis device, a bone plate is secured to a bone with at least two bone screws and the bone screws serve to bear and receive two rods, via which the correction and stabilization of the bones takes place.

31 Claims, 4 Drawing Sheets

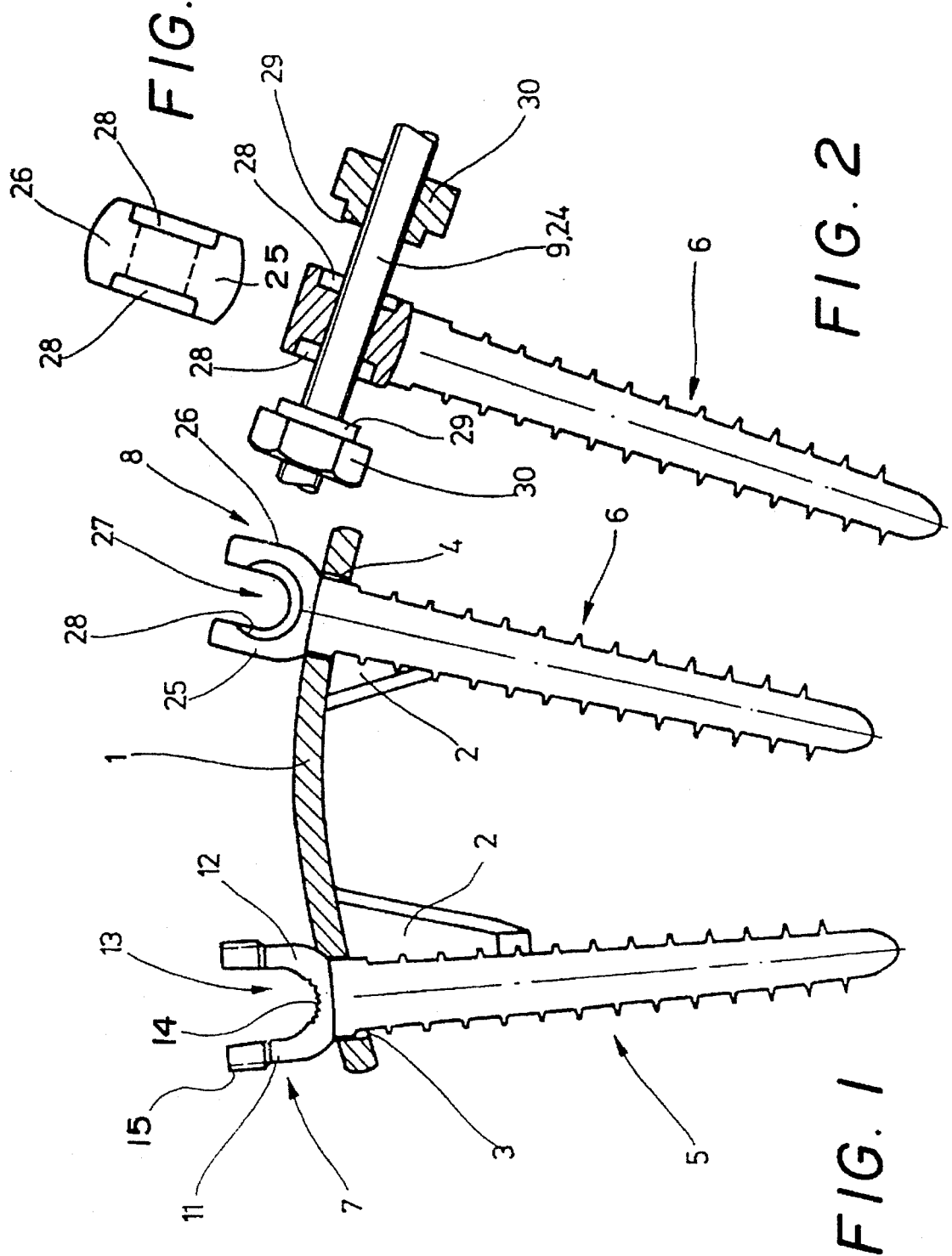

Fig. 7
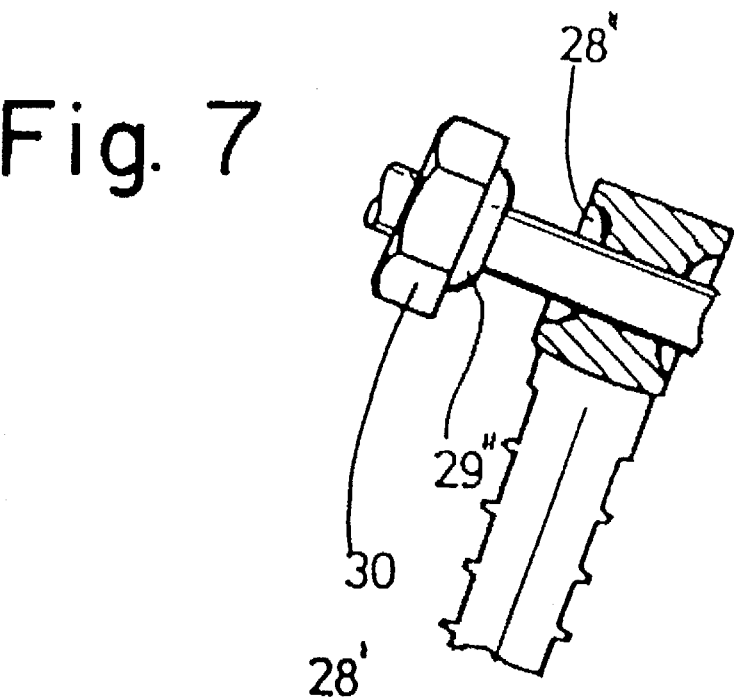
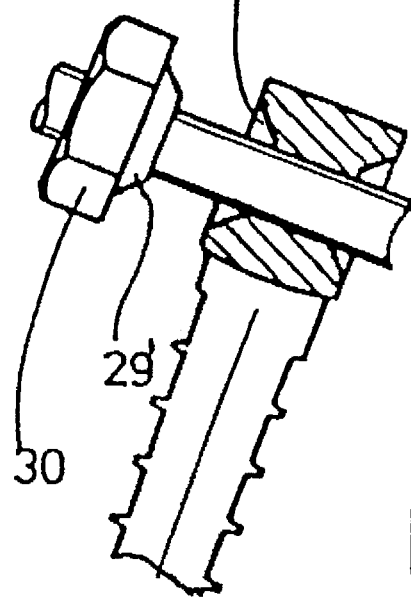
Fig. 8

OSTEOSYNTHESIS DEVICE

BACKGROUND OF THE INVENTION

1. Field of the Invention

The present invention relates to an osteosynthesis device with at least two bone screws, which can be secured to a vertebra of a spinal column; each bone screw has a screw head, on which or with which a rod can be secured and the two rods are connected to each other via a cross connecting device.

2. Prior Art

Osteosynthesis devices of the kind noted above are well known. They serve on the one hand to correct, stabilize, or stiffen bones. For example, German Patent 26 49 042 C2 discloses a shim, which rests upon the bone and is fixed by means of a bone screw. This bone screw is furthermore embodied as a retainer for a threaded rod, which serves as a correction rod. The force introduced into the bone via the threaded rod, the bone screw, and the shim is distributed onto the bone via the shim and effects a correction of the position of the bone. A bone corrected in this manner, though, requires stabilizing, which requires securing a further stabilizing element to the bone. This stabilizing element may, under some circumstances, have to be secured to another place on the bone, which makes a further operation necessary.

Further osteosynthesis devices are known from DE 31 21 271 C2, DE 39 16 198 A1, DE 41 10 002 C1, DE 41 07 480 A1, EP 443 892 A1, CH 672 420 A5, GB 2,178,323 A, CA 1,304,267 A, U.S. Pat. No. 5,030,220, DE 36 42 067 A1, EP 465 158 A2, EP 348 272 A1, and EP 346 521 A1. In the latter reference, it can clearly be seen that individual vertebrae of a spinal column are connected to one another via a number of bone screws and two rods. In this manner, the individual vertebrae can in fact be corrected, but not stabilized. Additional elements are required for stabilizing, which elements are disposed as lateral connectors between the two rods, as is known for example from EP 348 272 A1. Systems of this kind, however, are only partially suited to correct the positions of individual vertebrae, which as a rule, is carried out by pressing adjoining vertebrae against one another.

U.S. Pat. No. 4,289,123 discloses a device with which vertebrae can be displaced parallel via two threaded rods. With this device even a slight rotation of individual vertebrae is not possible. In addition a stabilizing of the vertebrae is only possible in part since they can move in the plane of the disks between vertebrae.

SUMMARY OF THE INVENTION

Taking European Patent 348 272 A1 as its point of departure, the object of the present invention, therefore, is to provide a simple osteosynthesis device with which a three dimensional correction, for example, of individual vertebrae of a spinal column or of the misalignment of individual vertebra bodies in comparison to one another is possible. The osteosynthesis device should additionally be primarily stable; that is, an achieved correction and stabilization as a rule should be load stable without further internal and external fixing mechanisms. This means that after the wound has finished healing, the spinal column corrected and stabilized in this manner stands up to the physiological demands.

This object is attained according to the present invention in that only one of the rods is embodied as an active, variably adjustable rod. This active rod serves as the correction rod via which the position and alignment of the individual vertebra is brought about. The other rod serves exclusively to stabilize the corrected position of the vertebra; the two rods are connected to each other via the cross connecting device. The purpose of the connection of the two rods via the cross connecting device is so that the forces occurring during stabilization of the vertebrae are transferred essentially onto the stabilizing rod. In addition the anchoring of each rod directly in the screw head of the bone screw has the essential advantage that the correction and stabilization forces are introduced directly into the bone.

In an embodiment according to the present invention, the cross connecting device is embodied as a bone plate with at least two securing bores for receiving two bone screws. In this embodiment form, the correction and stabilization forces are transferred via the bone plate between the two rods; in addition, the plate assumes the distribution of the tensile, compressive, and shear forces as well as the moments onto the bone. The osteosynthesis device according to the present invention is suited for correcting the individual bones over a wide range of misalignment relative to one another and for stabilizing them at the same time. It is primarily stable. After the application, which is preferably effected ventrally, it needs no further operation, e.g. for stabilization.

In one embodiment, the active rod is embodied as a threaded rod. This threaded rod is best suited for transferring correction forces produced onto individual vertebra bodies. In addition, the threaded rod can be adjusted smoothly in the longitudinal direction.

A further embodiment of the active rod provides that it is provided with a grid pattern. This grid pattern, in the form of a row of teeth or holes, or circumferential grooves or the like, guarantees that the active forces for mobilizing the vertebra bodies can be reliably introduced into the rod and transferred from it to the vertebra body. A positional correction can be achieved, for example, also by tilting the adjusting elements on the active rod.

The threaded rod, for example, can be advantageously secured on the screw head of the bone screw via two nuts. This system is known in bone screws. Bone plates are secured to the bone and a threaded rod is fixed via bone screws of this kind. Via the nuts, the threaded rod can be shifted in a purposeful way, and as a result individual bones or vertebrae can be actively corrected and even rotated, swiveled, or displaced. The active or threaded rod constitutes the dynamic part of the osteosynthesis device.

According to a preferred exemplary embodiment, the screw head has protrusions around the receiving opening for the threaded rod, which extend in the axial direction of the threaded rod, and the nut has recesses which receive the protrusions. In another exemplary embodiment, the screw head has recesses around the receiving opening for the threaded rod, which extend in the axial direction of the threaded rod, and the nut has protrusions which engage the recesses. The anchoring of the nuts on the screw head via protrusions and recesses has the essential advantage that the threaded rod is not only fixed in the axial direction in the screw head, which is embodied as fork-shaped, but is also reliably secured against slipping out. The recesses and protrusions can be embodied essentially as having the shape of a truncated cone, rectangle, or ball. The recess is always concave and the protrusion is always convex, but congruently with one another in each case.

In a further embodiment it is provided that the screw head has an external thread for a fixing device which can be screwed on. This fixing device closes the fork head and in this way secures the inserted rod on the one hand against an axial movement and on the other hand against a rotation in the position of the fork head. Naturally the fixing device also prevents the rod from falling out of the fork head.

A preferred exemplary embodiment provides that the fixing device is embodied as a union nut, acorn nut, or cap nut. In this manner the two legs of the fork head are secured against splaying, and the fork head is closed in a simple manner and the rod inserted in it is securely held. Other fixing devices are conceivable. Preferably the acorn nut is provided with a fixing screw, which can be screwed in coaxially, particularly with an internal hex and/or an annular cutting edge. After screwing on the acorn nut, the fixing screw can be adjusted via the internal hex and screwed onto the inserted rod in such a way that the annular cutting edge digs into the material of the fixing rod. In this manner, securing is achieved against both axial motion and rotation.

Preferably, one of the rods is embodied as a rod with longitudinal grooves. In addition, the screw head of a bone screw can be embodied in such a way that the base of the fork head is provided with longitudinal slots without undercuts into which the rod provided with the longitudinal grooves can be inserted. An additional rotational securing of this rod around its longitudinal axis is achieved by the longitudinal slots in the fork head and the longitudinal grooves in the rod. This rod constitutes the static or passive part of the osteosynthesis device.

According to a preferred exemplary embodiment, the diameters of the rods are of different sizes; in particular, the diameter of the threaded rod is smaller than that of the other rod. By means of the active rod with the smaller diameter, its flexibility compared to the other rod is increased in a simple manner so that the positions of the individual vertebra bodies to one another can be corrected without trouble using the active rod, as a result of its deformation. A high flexibility can also be achieved by choosing a suitable permissible material, whether metal, synthetic, or a combination.

Advantageously, the threaded rod is a correction rod and the other rod serves to stabilize the system. Thus the desired position of the individual bones is first adjusted via the threaded rod and this position is then fixed or stabilized with the other rod. As a result, the system according to the present invention is primarily stable.

Preferably the securing bores run orthogonal to the bone plate and/or oblique to it. In this manner, the bone screws converge or diverge in the desired direction due to the bone plate gripping onto the doming of the bone surface so that the bone plate or the osteosynthesis device can still be reliably secured, even with relatively small bones. Advantageously, the bone screws can now be screwed into the vertebrae in such a way that there is a large enough spacing from the marrow and that the rounded tip of the screw and a thread occur again on the other side of the bone.

According to the present invention, the securing bores each have a ball-shaped bearing for the screw head of the bone screw. As a result, the possibility is attained that the bone screw need not be screwed in strictly orthogonal to the bone plate, but can assume a slightly oblique position so that independent of the position of the bone plate, the screw shaft can be screwed into the region of the bone in which it can find an optimal hold. In addition, the ball-shaped bearing serves to receive lateral forces from the bone screw onto the bone plate or vice versa.

Preferably the two rods are disposed essentially parallel to each other. This is particularly advantageous when using the osteosynthesis device on spinal columns since in this manner, several bone plates in succession can be secured each respectively to one vertebra.

Further advantages, characteristics, and details of the present invention are revealed in the following description in which, with reference to the drawing, a particularly preferred exemplary embodiment is shown in particular. The characteristics shown in the drawing and mentioned in the description can be realized in the present invention individually or in an arbitrary combination.

BRIEF DESCRIPTION OF THE DRAWINGS

FIG. 1 shows a cross section through a bone plate with two bone screws inserted in the bone plate;

FIG. 2 shows a side view of the bone screw shown on the right in FIG. 1;

FIG. 3 shows a top view of the bone screw in FIG. 2;

FIG. 7 is a partial view similar to FIG. 2 showing the ball connection; and

FIG. 8 is a partial view similar to FIG. 2 showing the truncated cone connection.

DESCRIPTION OF THE PREFERRED EMBODIMENT

Figure 5:
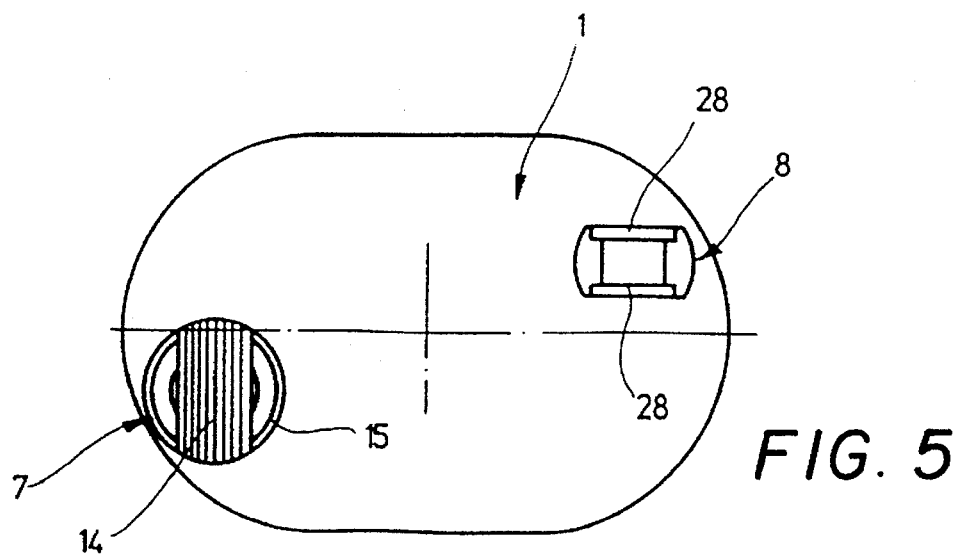
FIG. 5 shows a top view of the bone plate according to FIG. 1.

FIG. 1 shows a lateral connecting device in the form of a bone plate indicated by 1. On the proximal side (underside) of the bone plate 1, several anchoring pins 2 are provided, of which merely two are shown partially covered in FIG. 1. The bone plate 1 can be anchored to the bone secured against motion via the anchoring pins 2, which are hammered into the bone. It is further visible in FIG. 1 that the bone plate 1 has two securing bores 3 and 4, into each of which a bone screw 5 and 6 is inserted. Preferably the two securing bores 3 and 4 are disposed opposite each other with reference to the center of the bone plate 1, which can be seen in FIG. 5. The securing bores 3 and 4 can have a ball-shaped bearing in which the lower part of the screw head 7 or 8 of the bone screw 5 or 6 is supported. This lower part of the screw head 7 or 8 is then embodied correspondingly spherically so that it is received by this bearing with a positive fit. It can be further seen from FIG. 1 that the right bone screw 6 is aligned essentially orthogonal to the surface of the bone plate 1, i.e. essentially radial to its curvature. The bone screw 5 is positioned obliquely and extends essentially parallel to the axis of symmetry of the bone plate 1.

Figure 4:
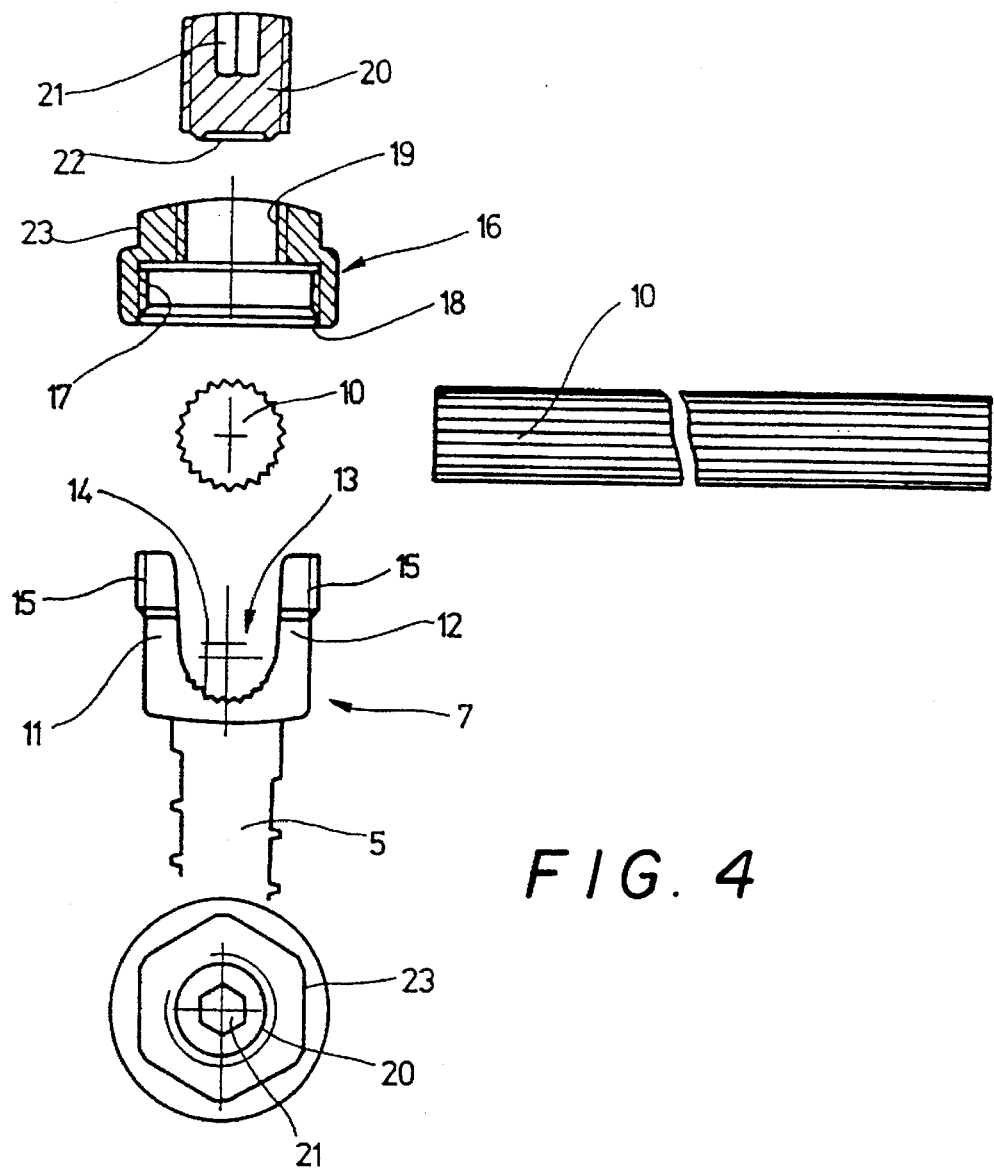
FIG. 4 shows an exploded view of the upper part of the bone screw shown on the left in FIG. 1 with the rod to be inserted, an acorn nut, and a fixing screw.

The two bone screws 5 and 6 are provided with different screw heads 7 and 8 so that different rods 9 and 10 (FIGS. 2 and 4) can be received. The bone screw 5 shown on the left in FIG. 1 is provided with a fork-shaped screw head 7, which has two legs 11 and 12. This fork-shaped screw head 7 is shown further in FIG. 4. The two legs 11 and 12 constitute between themselves a receiving opening 13 for the rod 10, which is embodied as a rod with longitudinal grooves. The base of the receiving opening 13 is provided with longitudinal slots 14, which have no undercuts, into which slots the rod 10 can be inserted. The longitudinal slots 14 correspond to the longitudinal grooves of the rod 10 and prevent a rotation of the rod 10 in the receiving opening 13. To fix the rod 10 in the receiving opening 13, the two legs 11 and 12 are provided with an external thread 15 on their outsides so that an acorn nut 16, which has a corresponding internal thread 17, can be screwed on. On its lower end, the acorn nut 16 has a centering collar 18, which makes screwing the acorn nut 16 onto the thread 15 easier. Coaxial to the internal thread 17, the acorn nut 16 is provided with a further internal thread 19 which has a smaller diameter. A fixing screw 20, which is embodied as a grub screw, can be screwed into this internal thread 19. On its upper end, this fixing screw 20 has an internal hex 21 and is provided with an annular cutting edge 22 on its underside. This annular cutting edge 22 digs into the rod 10 when the fixing screw 20 is tightened. The upper end of the acorn nut 16 and the upper end of the fixing screw 20 are embodied as ball-shaped and the acorn nut 16 has an external hex 23 as a tool engaging surface, via which the acorn nut 16 can be screwed onto the bone screw 5 and tightened.

The bone screw 6 shown on the right in FIG. 1 likewise has a fork-shaped screw head 8, into which a rod 9 embodied as a threaded rod 24 can be inserted. The screw head 8 here likewise has two legs 25 and 26, which between themselves constitute a receiving opening 27 (FIG. 3) into which the threaded rod 24 can be inserted. A recess 28 in the shape of a cylinder (FIG. 2), a truncated cone or a ball shape extending around the receiving opening (FIG. 9) Protrusions 29, which are provided on the face ends of nuts 30, which are screwed onto the threaded rod 24, engage in these recesses 28 of the screw head 8. Via these nuts 30, both the axial position of the threaded rod 24 in the screw head 8 of the bone screw 6 is fixed and the threader rod 24 is secured against an axial motion, rotation around its axis, and slipping out from the screw head 8.

Figure 6:
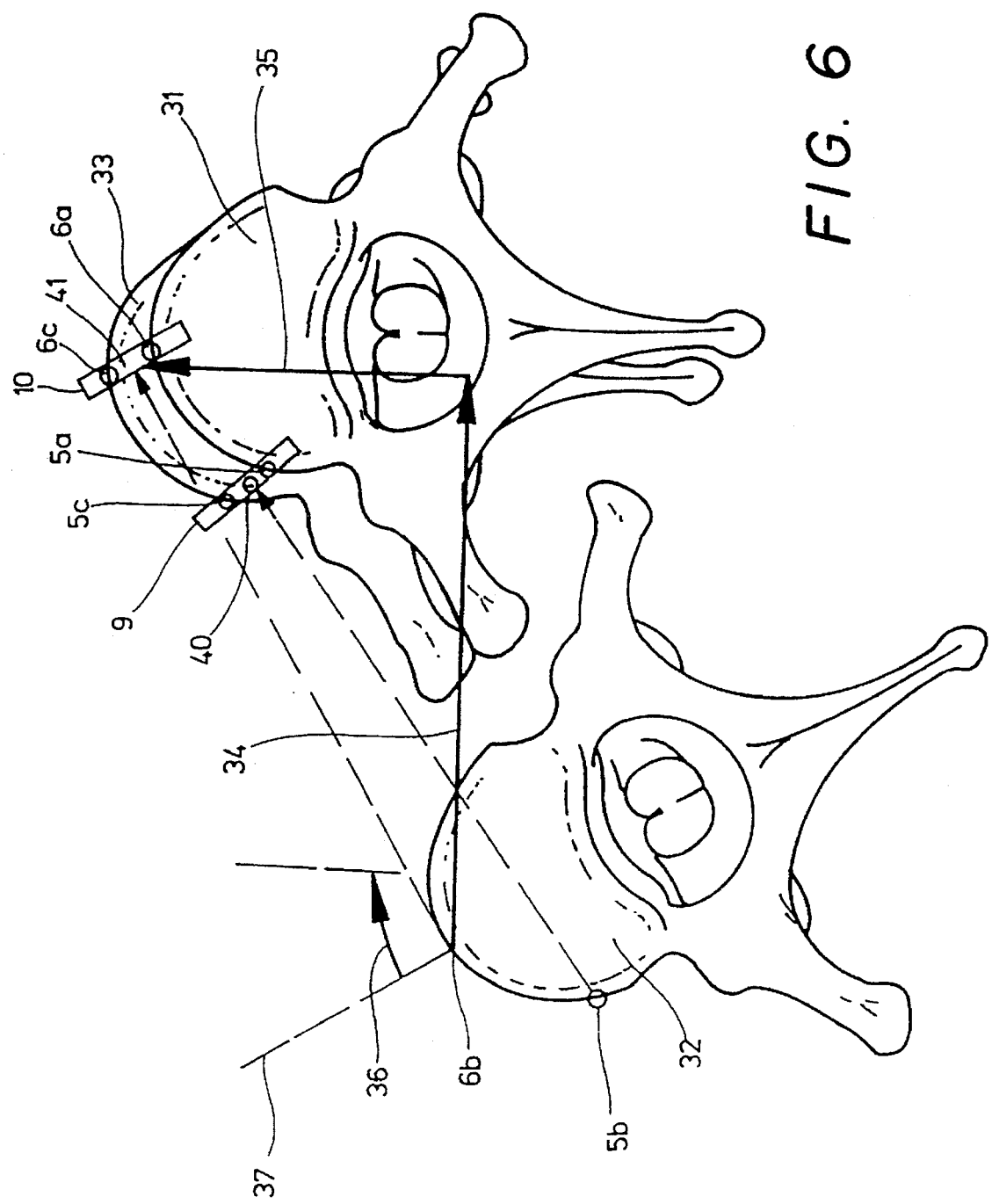
FIG. 6 shows a schematic representation of the shifting of a vertebra bone.

FIG. 6 shows three vertebra bodies 31–33; the vertebra body 32 is misaligned. The active rod 9 shifts this vertebra body 32 frontally in the direction of the arrow 34 and sagittally in the direction of the arrow 35 and rotates it in the direction of the arrow 36 (three dimensional directional change). By translation the vertebra body 32 is brought into line between the two vertebra bodies 31 and 33 and aligned by rotation so that its main axis 37 is aligned parallel, or at least approximately parallel, to that of the vertebra bodies 31 and 33. The bone screws are schematically represented by the reference numerals 5a–5c and 6a–6c, and the rods are schematically represented by the reference numerals 9 and 10. After correction, the bone screws 5b and 6b are situated at 40 and 41, i.e. between the bone screws 5a and 5c or 6a and 6c. In this position the vertebra bodies 31–33 are fixed against one another with the rod 10.

We claim:

1. An osteosynthesis device which can be secured to a vertebra of a spinal column, comprising: at least two bone screws for securing said device to the vertebra; at least two elongated rods of different diameter; and a cross connecting device mounted by said screws to the vertebra, wherein said cross connecting device extends substantially transverse to said elongated rods, wherein only one of said rods is embodied as an active, variably adjustable threaded rod, and the other rod is embodied as one of a milled and longitudinally grooved rod.

2. The osteosynthesis device of claim 1, wherein the cross connecting device is embodied as a bone plate with at least two securing bores for receiving two bone screws.

3. The osteosynthesis device of claim 1, further comprising: two nuts associated with at least one of said bone screws, wherein said threaded rod associated with said at least one of said bone screws can be secured on the screw head of said at least one of said bone screws via its associated nuts.

4. The osteosynthesis device of claim 3, wherein each screw head has a receiving opening, and wherein one of the screw heads has protrusions extending in the axial direction of its associated threaded rod around its associated receiving opening, and its two associated nuts have recesses which receive the protrusions.

5. The osteosynthesis device of claim 4, wherein the recesses and protrusions are embodied substantially in the shape of at least one of a truncated cone, a cylinder, or a ball.

6. The osteosynthesis device of claim 3, wherein each screw head has a receiving opening, and wherein one of the screw heads has recesses extending in the axial direction of its associated threaded rod around its associated receiving opening, and its associated nuts have protrusions which engage in the recesses.

7. The osteosynthesis device of claim 1, wherein the screw head is embodied as fork-shaped.

8. The osteosynthesis device of claim 1, wherein the screw head has an external thread for receiving a fixing device screwed thereon.

9. The osteosynthesis device of claim 8, wherein the fixing device is embodied as one of a union nut and acorn nut.

10. The osteosynthesis device of claim 9, wherein the acorn nut is provided with a fixing screw, which can be screwed in coaxially, said fixing screw having an internal hex and an annular cutting edge.

11. The osteosynthesis device of claim 1, wherein there are two bone screws, and wherein the active rod associated with one bone screw is a correction rod and the other rod associated with the other bone screw serves for stabilization.

12. The osteosynthesis device of claim 1, wherein the securing bores run according to one of an orthogonal or oblique direction to the bone plate.

13. The osteosynthesis device of claim 1, wherein said cross connecting device has at least two securing bores, said securing bores each having a ball-shaped bearing for its associated screw head.

14. The osteosynthesis device of claim 1, wherein there are two rods and the two rods are disposed essentially parallel to each other.

15. The osteosynthesis device of claim 1, wherein the diameter of the threaded rod is smaller than that of the other rod.

16. The osteosynthesis device of claim 1, wherein said active, variably adjustable threaded rod is constructed to have a greater flexibility than the other rod.

17. The osteosynthesis device of claim 1, wherein there are two rods and the two rods are comprised of different materials.

18. The osteosynthesis device of claim 1, said device being adapted for ventral application.

19. The osteosynthesis device of claim 1, wherein one rod is embodied for variable transfer of tensile and compressive forces acting essentially in the axial direction of the rod.

20. The osteosynthesis device of claim 1, wherein one rod is embodied for transferring moments acting in that orthogonal plane of a rod and which has no dynamic properties with regard to the vertebrae.

21. The osteosynthesis device of claim 1, wherein one rod is embodied as the dynamic part and one rod is embodied as the static part of the osteosynthesis device.

22. The osteosynthesis device of claim 1, wherein the rods have a configuration which is one of circular, oval, rectangular, triangular, or other polygonal cross section or a combination thereof.

23. A system of at least two osteosynthesis devices which can be secured to a vertebra of a spinal column, each osteosynthesis device comprising: at least two bone screws for securing said device to the vertebra; at least two elongated rods of different diameter; and a cross connecting device mounted by said screws to the vertebra, wherein said rods extend between each of the osteosynthesis devices, said cross connecting device extends substantially transverse to said elongated rods and only one of said elongated rods is embodied of an active, variably adjustable threaded rod, and the other rod is embodied as one of a milled and longitudinally grooved rod.

24. The osteosynthesis device of claim 23, wherein the cross connecting device is embodied as a bone plate with at least two securing bores for receiving two bone screws.

25. The osteosynthesis device of claim 23, further comprising: two nuts associated with at least one of said bone screws, wherein said threaded rod associated with said at least one of said bone screws can be secured on the screw head of said at least one of said bone screws via its associated nuts.

26. The osteosynthesis device of claim 25, wherein each screw head has a receiving opening, and wherein one of the screw heads has protrusions extending in the axial direction of its associated threaded rod around its associated receiving opening and its two associated nuts have recesses which receive the protrusions.

27. The osteosynthesis device of claim 25, wherein each screw head has a receiving opening, and wherein one of the screw heads has recesses extending in the axial direction of its associated threaded rod around its associated receiving opening and its associated nuts have protrusions which engage in the recesses.

28. The osteosynthesis device of claim 23, wherein there are two bone screws, and wherein the active rod associated with one bone screw is a correction rod and the other rod associated with the other bone screw serves for stabilization.

29. The osteosynthesis device of claim 23, wherein the securing bores run according to one of an orthogonal or oblique direction to the bone plate.

30. The osteosynthesis device of claim 23, wherein said cross connecting device has at least two securing bores, said securing bores each having a ball-shaped bearing for its associated screw head.

31. The osteosynthesis device of claim 23, wherein there are two rods and the two rods are disposed essentially parallel to each other.

* * * * *

UNITED STATES PATENT AND TRADEMARK OFFICE
Certificate

Patent No. 5,643,261                                         Patented: July 1, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Bernd Schäfer, Schorndorf, Germany; Klaus Zielke, Wildungen, Germany; and Henry Halm, Bissendorf-Wissingen, Germany.

Signed and Sealed this Sixteenth Day of March 2004.

*MICHAEL MILANO*
*Supervisory Patent Examiner*
Art Unit 3731